US00PP19033P2

(12) United States Plant Patent
Egger

(10) Patent No.: US PP19,033 P2
(45) Date of Patent: Jul. 15, 2008

(54) ***HEUCHERA* PLANT NAMED 'LEMON CHIFFON'**

(50) Latin Name: *Heuchera hybrida*
Varietal Denomination: Lemon Chiffon

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/805,648

(22) Filed: May 23, 2007

(51) Int. Cl.
*A01H 5/00* (2006.01)

(52) U.S. Cl. ..... Plt./440
(58) Field of Classification Search ..... Plt./440
See application file for complete search history.

*Primary Examiner*—Kent L. Bell
*Assistant Examiner*—Annette H Para
(74) *Attorney, Agent, or Firm*—Klarquist Sparkman, LLP

(57) ABSTRACT

A new and distinct *Heuchera* plant substantially as shown and described, characterized by yellow spring leaves, chartreuse leaves in summer, fall and winter, small, light coral pink colored flowers, and good vigor.

1 Drawing Sheet

Botanical denomination: *Heuchera hybrida.*
Variety designation: 'Lemon Chiffon'.

Cross reference to siblings: *Heuchera* 'Lime Rickey' (U.S. Plant Pat. No. 16,210), and *Heuchera* 'TNHEU042' Key Lime Pie (U.S. Plant Pat. No. 16,735).

The present invention relates to a new and distinct cultivar of *Heuchera hybrida* and given the cultivar name of 'Lemon Chiffon'. *Heuchera* is in the family Saxifragaceae. *Heuchera* 'Lemon Chiffon' originated from a cross between *Heuchera* 'Amber Waves' (U.S. Plant Pat. No. 13,348), as the seed parent, and *Heuchera* 'Huntsman', an unpatented plant, as the pollen parent. Given its ornamental foliage and flower form it is probable that *Heuchera micrantha, H. americana, H. brizoides,* and *H. sanguinea* are in its parentage.

This new *Heuchera* is distinguished by:

1. Yellow spring leaves.
2. Chartreuse leaves in summer, fall, and winter.
3. Small light coral pink colored flowers.
4. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the bloom and summer through winter foliage of *Heuchera* 'Lemon Chiffon'.

FIG. 2 shows a one year old plant of *Heuchera* 'Lemon Chiffon' growing in the ground in the shade house in May in Canby, Oreg.

DETAILED PLANT DESCRIPTION

The following is a detailed description of the new *Heuchera* cultivar based on observations of a four-year-old specimen grown in a 5 gallon container in a cool greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—24 cm tall from top of the foliage to the ground and 59 cm wide.
*Habit.*—Mounding.
*Vigor.*—Excellent.
*Roots.*—Fibrous, freely branching, fine, and white in color. Roots develop easily from stem cuttings.

Leaf:

*Type.*—Simple.
*Arrangement.*—Rosette.
*Shape.*—Ovate.
*Lobing/division.*—5 main lobes, with 2 shallow secondary lobes.
*Venation.*—Palmate.
*Margins.*—Crenate.
*Apex.*—Mucronulate.
*Base.*—Cordate, lobes overlapping and curling up at the base.
*Blade size.*—8 to 10 cm long and 7 to 8.5 cm wide.
*Surface texture.*—Glandular hairs on both sides.
*Petiole description.*—Grows to 18 cm long and 3.5 mm wide, with long and short glandular hairs, Greyed Yellow 160A.
*Leaf color.*—Spring newest growth, topside, Yellow 9C; bottom side, Yellow Green 144D; summer and winter topside, Yellow Green 145A; bottom side Yellow Green 144D.

Inflorescence:

*Size.*—16 cm long and 5.5 cm wide.

*Type.*—Thyrse.

*Number of flowers per thyrse.*—65 to 110 per thyrse.

*Number of thyrse.*—38 in first spring flush.

*Peduncle.*—45 to 50 cm tall, 2 mm wide at base, Yellow Green 153B, glandular hairs, with 1 to 3 petiolate cauline leaves (ovate, blades 1 to 4 cm long and 1 to 3 cm wide with a lobed and incised margin, acute tip, cordate base, and glandular hairs).

*Pedicel.*—Variable in size, with glandular hairs, Greyed Red 182B.

*Bloom period.*—Late April to June in Canby, Oreg.

Flower bud:

*Size.*—3 mm wide and 4 mm long.

*Description.*—Glandular puberulent, ovoid.

*Color.*—Orange Red 35C in the middle with the tip Red 52D and base Yellow Green 154D.

Flower:

*Type.*—Perfect.

*Shape.*—Campanulate.

*Size.*—5 mm long and 6 mm wide.

*Petal description.*—5 in number, inconspicuous, 2 mm long, lanceolate, tip acute, base attenuate, margin entire, sparsely glandular on back, Red Purple 62C on both sides.

*Calyx description.*—5 mm long and 6 mm wide, with 5 lobes, divided ⅓ way to the base, glandular hairs on both sides, tip acute, margin entire, color on both sides of the tube is Red 36B, lobes are Red Purple 62C with Greyed Red 182A on the tip.

*Stamen description.*—5 in number, 3 mm long, filaments White 155A, anthers 0.5 mm, oval, Orange Red 32C, pollen Yellow 19A.

*Pistil description.*—1, 4 mm long, ovary 2 mm long and 1.5 mm wide, Yellow Green 154C, style 2 mm long, White 155B, stigma two-branched, White 155B.

*Fragrance.*—None.

*Lastingness.*—Each thyrse blooms for about 2 weeks on the plant.

Fruit:

*Type.*—Two-beaked ovoid capsule.

*Size.*—3.5 mm deep by 5 mm wide.

*Fertility.*—Good.

*Color.*—Brown 200D.

Seed:

*Shape.*—Linear.

*Size.*—2 mm long.

*Color.*—Black, RHS 202A.

Disease and pest tolerance: No known resistance to rust, a common problem with light leaf type *Heuchera.* Excellent disease tolerance to powdery mildew. All *Heuchera* are susceptible to root weevils.

COMPARISON TO SIMILAR *HEUCHERA*

Compared to its sibling, *Heuchera* 'Lime Rickey' (U.S. Plant Pat. No. 16,210), this new variety has spring foliage that is yellow maturing to chartreuse rather than chartreuse spring foliage maturing to lime colored, light pink flowers rather than white, and leaves that are not ruffled, rather than ruffled.

Compared to its sibling, *Heuchera* 'TNHEU042' Key Lime Pie (U.S. Plant Pat. No. 16,735)), this new variety has spring growth that is yellow maturing to chartreuse rather than chartreuse spring foliage maturing to lime colored.

I claim:

1. A new and distinct *Heuchera* plant as herein illustrated and described.

* * * * *

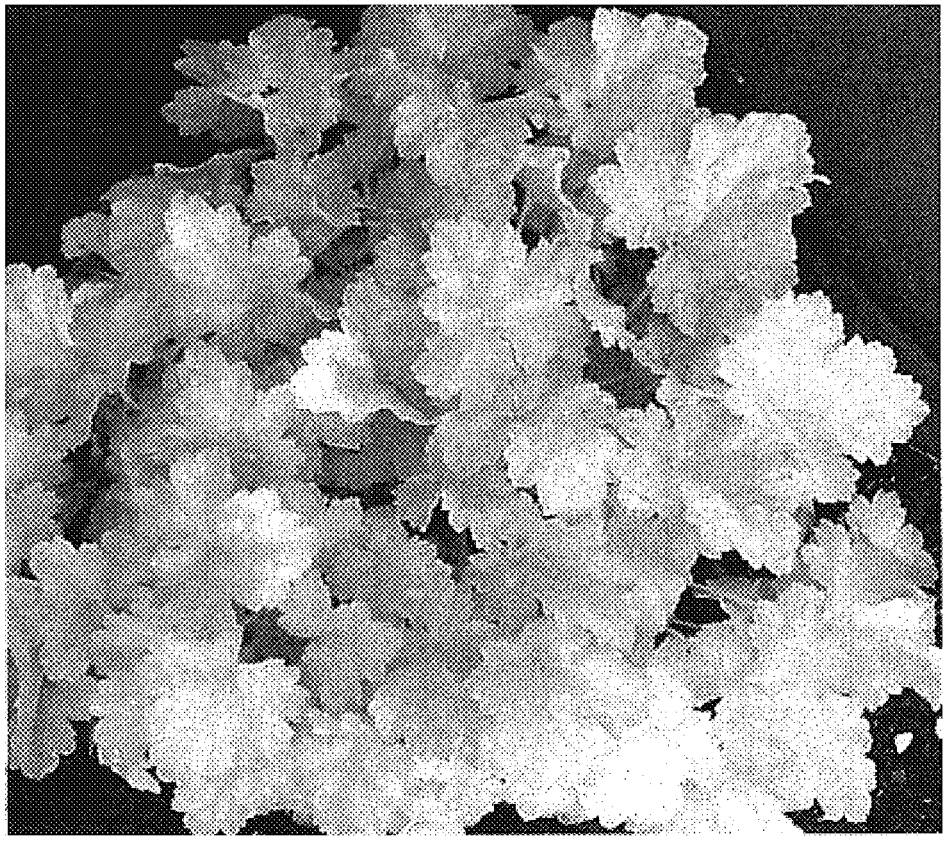

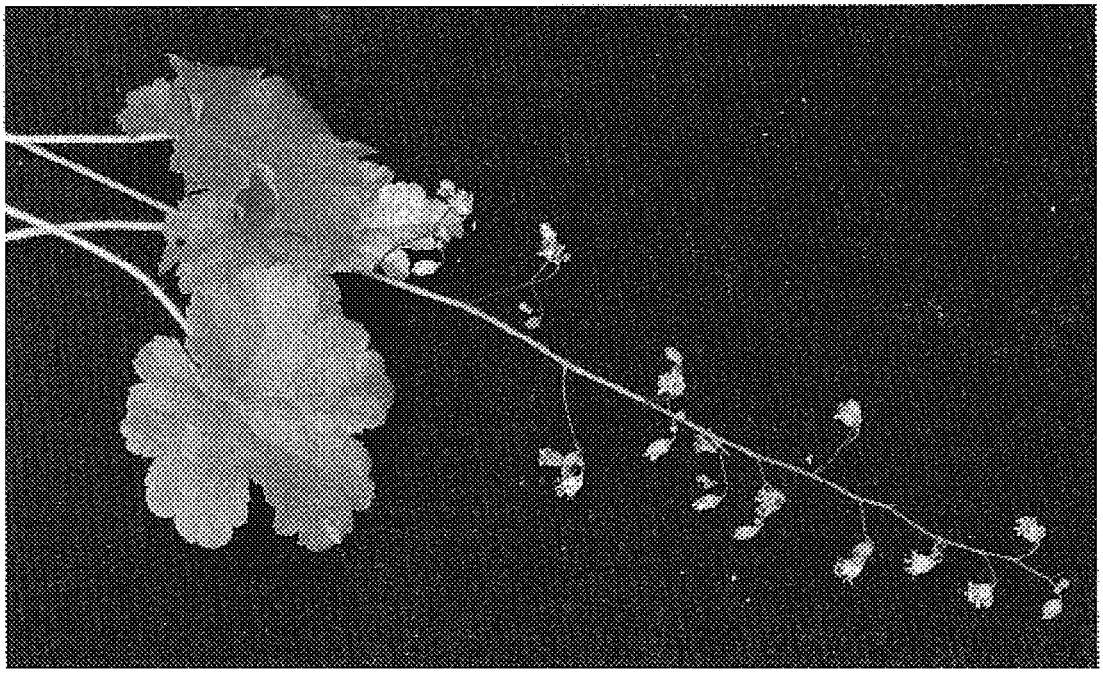
Figure 1 above, Figure 2 below